United States Patent
Sugise et al.

(10) Patent No.: US 6,417,404 B1
(45) Date of Patent: Jul. 9, 2002

(54) PROCESS FOR CONTINUOUSLY PRODUCING A CYCLODODECANONE COMPOUND

(75) Inventors: Ryoji Sugise; Shuji Tanaka; Takashi Doi; Masayuki Nishio; Sadao Niida; Tsunao Matsuura, all of Ube (JP)

(73) Assignee: Ube Industries Ltd., Ube (JP)

( * ) Notice: Subject to any disclaimer, the term of this patent is extended or adjusted under 35 U.S.C. 154(b) by 0 days.

(21) Appl. No.: 09/879,067

(22) Filed: Jun. 13, 2001

(30) Foreign Application Priority Data

Jun. 14, 2000 (JP) ........................................ 2000-177851

(51) Int. Cl.[7] .............................................. C07C 45/00
(52) U.S. Cl. ...................................... 568/338; 568/361
(58) Field of Search .................................. 568/338, 361

(56) References Cited

U.S. PATENT DOCUMENTS 4,734,529 A    3/1988   Berg et al. ................... 568/310

FOREIGN PATENT DOCUMENTS

| DE | 3601380 A1 | 7/1987 |
| DE | 3744094 A1 | 7/1989 |
| SU | 407874 | 12/1973 |

OTHER PUBLICATIONS

L.I. Zakharkin et al., "Isomerization of Trans–1, 2–Epoxy–CIS, Trans–5,9–Cyclododecadiene, Trans–1, 2–Epoxy–Trans, Trans–5–9–Cyclododecadiene, and Trans–Epoxycyclododecane to the Corresponding Ketones by the Action of Lithium and Magnesium Iodides and Bromides", Zhurnal Organischeskoi Khimii, vol. 26, No. 7, pp. 1497–1500, Jul. 1990.

L.I. Zakharkin et al., "Isomerization of Trans–1,2–Eposy–Cis, Trans–5,9–Cyclododecadiene, Trans–1,2–Epoxy–Trans, Trans–5,9—Cyclododecadiene, and Trans–Epoxycyclododecane to the Corresponding Ketones by the Action of Lithium and Magnesium Iodides and Bromides", A.N. Nesmeyanov Institute of Heteroorganic Compounds, Academy of Sciences of the USSR, Moscow. Translated from *Zhurnal Organicheskoi Khimii*, vol. 26, No. 7, pp. 1497–1500, Jul., (1990).

*Primary Examiner*—Alan Siegel
(74) *Attorney, Agent, or Firm*—Morgan, Lewis & Bockius LLP

(57) ABSTRACT

A cyclododecanone compound is continuously produced by feeding a liquid feed containing a corresponding epoxycyclododecane compound and LiBr and/or LiI into a frontmost reaction region of a plurality of reaction regions connected to each other in series; successively passing the liquid feed through the series of reaction regions to catalytically isomerize the epoxycyclododecane compound into a corresponding cyclododecanone compound; and collecting the resultant reaction mixture containing the target cyclododecanone compound from a rearmost reaction region of the series of reaction regions.

13 Claims, 2 Drawing Sheets

PROCESS FOR CONTINUOUSLY PRODUCING A CYCLODODECANONE COMPOUND

BACKGROUND OF THE INVENTION

1. Field of the Invention

The present invention relates to a process for producing a cyclododecanone compound. More particularly, the present invention relates to a process for producing a cyclododecanone compound by catalytically isomerizing a corresponding epoxycyclododecane compound.

A cyclododecanone compound is useful as a material for producing laurolactam, dodecanedioic acid and dodecane diol.

2. Description of the Related Art

Methods for producing a cyclododecanone by isomerizing a corresponding epoxycyclododecane compound in the presence of a catalyst consisting of a lithium halide are known from a plurality of reports.

For example, German Patent No. 3,744,094 discloses an isomerization of an epoxycyclododecane in the presence of a catalyst consisting of lithium chloride in a reaction medium consisting of N-methylpyrrolidone or N,N'-dimethylethyleneurea to produce cyclododecanone with a yield of 94%.

Also, German Patent No. 3,601,380 discloses that, by isomerization of 1,2-epoxy-5,9-cyclododecadiene in the presence of a catalyst consisting of sodium iodide in a reaction medium consisting of a polyethylene glycol (NaI: 3 wt %, 195° C., 9 hours), cyclododeca-1,7-diene-1-one is produced with a yield of 98.7%.

In each of the above-mentioned methods, however, since a polar solvent is employed as a reaction medium, means for recovering the solvent or for decomposing the solvent must be added to the production system for the target compound and this causes the production cost of the target compound to increase.

Further, the reaction rate of the isomerization reaction is decreased by a dilution effect or a salvation effect of the solvent, and thus the reaction time necessary to effect the isomerization reaction at a conversion close to 100% becomes long. Also, since the reaction is carried out in a batch type reaction system, the above-mentioned methods are unsuitable for industrially producing the target compound in a large quantity with a high efficiency.

Further, SU Patent 407,874 discloses an isomerization reaction of an epoxycyclododecane, in the presence of a catalyst consisting of anhydrous LiBr, in no solvent. In examples of the SU patent, it is reported that when the reaction was carried out in an amount of LiBr of 4% by weight at a reaction temperature of 120 to 130° C. for a reaction time of 18 hours or in an amount of LiBr of 3.3% by weight at a reaction temperature of 200° C. for a reaction time of 3 hours, the target cyclododecanone was obtained at a yield of 100% or 83.3%.

In the former example, the reaction time is too long, and thus the reaction is not practical, and in the later example, the selection to the target compound is low and a by-product having a high boiling temperature was produced.

The high boiling temperature by-product is disadvantageous in that when the catalyst is recovered from the reaction mixture after the reaction is completed and recycled to the reaction procedure, the high boiling temperature by-product is accumulated in the reaction system to affect the reaction, and thus an additional procedure for removing the high boiling temperature by-product from the reaction mixture becomes necessary.

In this connection, it may be considered that for the purpose of increasing the reaction rate, the concentration of the catalyst in the reaction system should be increased. However, in the method of the former example, since the solubility of LiBr in the reaction system is saturated, the concentration of the catalyst cannot be increased. In the method of the later example, the reaction temperature is established at a high level to increase the reaction rate. This high temperature causes a side reaction to occur, the yield of the target compound to be decreased, and the high boiling temperature by-product to be produced.

Further, Zh. Org. Khim (1990), 26(7), 1497–1500, discloses that when an isomerization reaction of an epoxycyclododecane was carried out in the presence of 2.3 molar % of a catalyst consisting of LiBr (lithium bromide) at a reaction temperature of 150° C. for a reaction time of 10 hours, the target cyclododecanone was obtained at a yield of 96.6%, and when the reaction of the epoxycyclododecane was effected in the presence of 1.5 molar % of LiI (lithium iodide) at 150° C. for 5 hours, the target cyclododecanone was obtained at a yield of 91.2%. In the case of this report, however, it is assumed that to make the conversion of the epoxycyclododecane close to 100%, a very long reaction time is necessary. Also, the reaction of the report was effected in a batch-type reaction system, and thus no continuous method for the reaction is disclosed in the report.

In the case where a cyclododecanone compound is produced by isomerizing an epoxycyclododecane compound, since the boiling temperature of the epoxycyclododecane compound is approximately equal to that of the cyclododecanone compound, there are many cases in which the separation of the two compounds from each other by distillation is very difficult from an industrial point of view. Also, since the two compounds are similar in physical and chemical properties to each other, the separation on refining of the two compounds by crystallization or extraction is difficult. Therefore, to produce the cyclododecanone compound with a high degree of purity, it is necessary that the conversion of the epoxycyclododecane compound is controlled to approximately 100%. For this purpose, it is possible to increase the reaction temperature or the content of the catalyst.

However, as mentioned above, an increase in the reaction temperature causes frequent occurrence of side reactions and thus the production of the high boiling temperature compounds is promoted and the yield of the target cyclododecanone compound is reduced.

On other hand, as a measure to enhance the conversion of the epoxycyclododecane compound, it is possible to increase the content of the catalyst in the reaction system. However, the increase in the catalyst content may cause a difficulty in the dissolution of the catalyst in the reaction system and may make the cost of the reaction increase. Thus, this measure is not practical.

All of the reaction procedures of the above-mentioned prior arts are carried out in batch type reactor systems and thus are disadvantageous in that the process operations are complicated, the safety of the operations is unsatisfactory and the operation cost is high. In fact, the isomerization reaction is an exothermic reaction. Therefore, when the cyclododecanone compound is industrially produced in a large quantity by the batch type reactor system, a large amount of heat is generated. In practice, it is important to remove the heat with a high efficiency. For example, when a large amount of an epoxycyclododecane compound is catalytically isomerized at a temperature of 200° C. in a batch type reactor, since the removal of the generated reaction heat is difficult, the reaction temperature may be rapidly increased to such an extent that a bumping of the liquid reaction mixture occurs.

As mentioned above, in the conventional technology, it has not yet been possible to isomerize the epoxycyclododecane compound in a short reaction time at a conversion of the compound of approximately 100% with a selectivity to the target compound of approximately 100%. Further, since the known isomerization method is carried out in a batch type reactor, the target cyclododecanone compound cannot be continuously and safely provided. Namely, a continuous process for producing the cyclododecanone compound in an industrial scale has not yet been established.

SUMMARY OF THE INVENTION

An object of the present invention is to provide a process for continuously producing a cyclododecanone compound in an industrial scale by an isomerization reaction of an epoxycyclododecane compound in the presence of a catalyst comprising lithium bromide and/or lithium iodide, in a relatively short reaction time, with a high conversion of the epoxycyclododecane compound with a high selectivity of the target cyclododecanone compound with high safety.

The above-mentioned object can be attained by the process of the present invention for continuously producing a cyclododecanone compound.

The process of the present invention comprises;

feeding a liquid reaction mixture comprising an epoxycyclododecane compound and a catalyst comprising at least one member selected from lithium bromide and lithium iodide into a frontmost reaction region of a plurality of reaction regions connected to each other in series;

successively passing the liquid reaction mixture through the series of reaction regions to catalytically isomerize the epoxycyclododecane compound to produce a corresponding cyclododecanone compound; and collecting the resultant reaction mixture containing the cyclododecanone compound from a rearmost reaction region of the series of reaction regions.

In the process of the present invention for continuously producing a cyclododecanone compound, the epoxycyclododecane compound is preferably selected from saturated and unsaturated cycloaliphatic compounds having 12 carbon atoms and provided with an epoxy group.

In the process of the present invention for continuously producing a cyclododecanone compound, the epoxycyclododecane compound is preferably selected from monoepoxycyclododecane, monoepoxycyclododecenes, monoepoxycyclododecadienes or monoepoxycyclododecatrienes.

In the process of the present invention for continuously producing a cyclododecanone compound, the temperature of a portion of the liquid reaction mixture located in a rear part of the series of reaction regions is preferably controlled to be equal to or higher than that in a front part of the series of reaction regions.

In the process of the present invention for continuously producing a cyclododecanone compound, the series of reaction regions are preferably constituted from a plurality of reaction vessels independent from each other and connected to each other in series in a manner such that with respect to a pair of front and back reaction vessels arranged adjacent to each other, the front vessel is connected to the back vessel through a conduit.

In the process of the present invention for continuously producing a cyclododecanone compound, a bottom portion of the front vessel is connected to a top portion of the back vessel through the conduit.

In the process of the present invention for continuously producing a cyclododecanone compound, the series of reaction regions are preferably constituted from a plurality of reaction chambers separated from each other and connected to each other in such a manner that, with respect to a pair of front and back reaction chambers arranged adjacent to each other, a top portion of the front vessel is connected to a top portion of the back vessel through a liquid path through which a portion of the liquid reaction mixture contained in the front vessel is allowed to overflow into the back vessel.

In the process of the present invention, for continuously producing a cyclododecanone compound, the series of reaction regions preferably comprise a plurality of reaction chambers separated from each other with partitions arranged between the reaction chambers and connected to each other in series through at least one hole formed in each of the partitions.

In the process of the present invention for continuously producing a cyclododecanone compound, at least one of the reaction regions is preferably sealed with an inert gas.

In the process of the present invention for continuously producing a cyclododecanone compound, the catalyst is preferably present in an amount of 0.01 to 20 molar % based on the molar amount of the epoxycyclododecane compound.

In the process of the present invention for continuously producing a cyclododecanone compound, the liquid reaction mixture in the series of reaction regions is heated at a temperature of 100 to 350° C.

In the process of the present invention for continuously producing a cyclododecanone compound, the temperature of a portion of the liquid reaction mixture located at the outlet portion of the rearmost reaction region is preferably controlled to 0 to 100° C. above that at the inlet portion of the frontmost reaction region.

In the process of the present invention for continuously producing a cyclododecanone compound, the liquid reaction mixture preferably passes through the series of reaction regions in a time of 0.1 to 24 hours.

DESCRIPTION OF THE PREFERRED EMBODIMENTS

Figure 1:
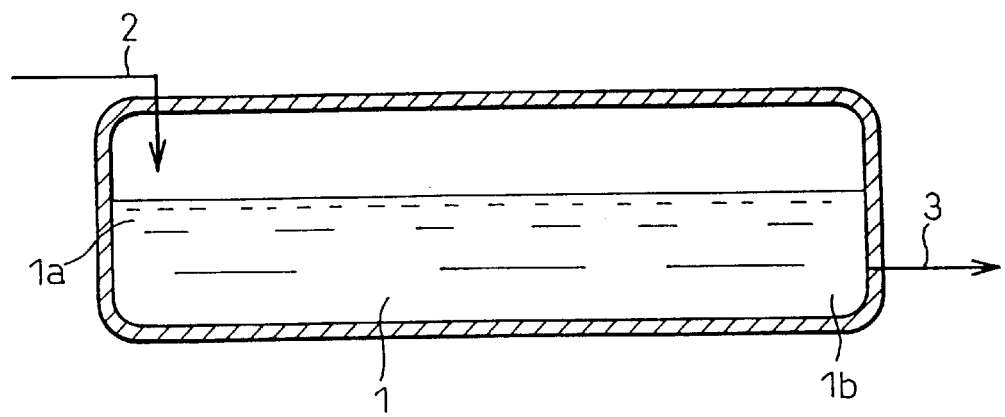
FIG. 1 is an explanatory cross-sectional view of a conventional isomerization reactor for producing a cyclododecanone from an epoxycyclododecane compound.

In the process of the present invention, a cyclododecanone compound is continuously produced by isomerizing an epoxycyclododecane compound corresponding to the target cyclododecanone compound in the presence of a catalyst. In this process, continuously, a liquid reaction mixture comprising an epoxycyclododecane compound and a catalyst comprising at least one member selected from lithium bromide and lithium iodide is fed into a frontmost reaction region of a plurality of reaction regions separated from each other and connected to each other in series through at least one liquid path; the fed liquid reaction mixture is successively passed through the series of reaction regions and the at least one liquid path to catalytically isomerize the epoxycyclododecane compound to produce a corresponding cyclododecanone compound; and the resultant reaction mixture containing the cyclododecanone compound is collected from a rearmost reaction region of the series of reaction regions. The collected reaction mixture contains the target cyclododecanone compound in a high yield.

The epoxycyclododecane compound usable for the process of the present invention includes saturated and unsaturated cyclohydrocarbon compounds having 12 carbon atoms and provided with an epoxy group, and is preferably selected from monoepoxycyclododecane, monoepoxycyclododecacenes, monoepoxycyclododecadienes, monoepoxycyclododecatrienes, more preferably from monoepoxycyclododecane and monoepoxycyclododecadienes. The above-mentioned epoxycyclododecane compounds include various isomers. For these isomers, there are no limitations on the positions of the epoxy group and the double bond contained therein.

Also, in the isomers, there is no limitation on the steroisomerism or the geometrical isomerism.

In the practice of the process of the present invention, the epoxycyclododecane compounds as mentioned above may be employed alone or in a mixture of two or more thereof.

The cyclododecanone compound obtained by the process of the present invention corresponds to the starting epoxycyclododecane compound, and preferably includes cyclododecanone, cyclododecenones, cyclododecadienones and cyclododecatrienones.

The catalyst usable for the process of the present invention comprises at least one member selected from lithium bromide and lithium iodide. A specific treatment for the catalyst before it is subjected to the process of the present invention is unnecessary. A usual commercially available lithium bromide and lithium iodide may be employed without pre-treatment. Preferably, the catalyst comprises at least one member selected from anhydrous lithium bromide, lithium bromide mono hydrate, lithium bromide dihydrate, lithium bromide trihydrate, anhydrous lithium iodide, lithium iodide monohydrate, lithium iodide dihydrate and lithium iodide trihydrate. These compounds may be continuously supplied in the state of a solid or in the state of a solution in an epoxycyclododecane compound and/or a cyclododecanone compound or in a non-polar solvent containing an epoxycyclododecane compound, to the series of reaction regions. Preferably, the catalyst is supplied in the state of a solution, in an epoxycyclododecane compound and/or a cyclododecanone compound, into the series of reaction regions.

There is no limitation to the amount of the catalyst contained in the liquid reaction mixture before the start of the reaction. The content of the catalyst in the reaction mixture is variable in response to the solubility of the catalyst in a reaction medium contained in the reaction mixture and the reaction conditions. Preferably, the catalyst is employed in an amount of 0.01 to 20 molar %, more preferably 0.1 to 5 molar %, per mole of the starting epoxycyclododecane compound. If the amount of the catalyst is too low, the necessary reaction time to complete the isomerization reaction may become too long and thus this may be not practical for industry. Also, if the catalyst is employed in too large an amount, it may cause the cost of the process to be too high and thus an economical disadvantage may occur.

In the process of the present invention, there is no limitation to the type of gas atmosphere in the reaction regions. Preferably, at least one region of the series of reaction regions is sealed with an inert gas. More preferably, all of the series of reaction regions are sealed with the inert gas. The inert gas preferably comprises at least one member selected from helium gas, neon gas, argon gas, hydrogen gas, nitrogen gas, carbon monoxide gas, carbon dioxide gas, methane gas and ethylene gas, more preferably from nitrogen gas and argon gas. These gases for the inert gas may be employed alone or in a mixture of two or more thereof.

In the process of the present invention, there is no limitation to the reaction temperature. Usually, the isomerization reaction of the epoxycyclododecane compound is preferably carried out at a temperature of 100 to 350° C., more preferably 120 to 300° C., still more preferably 150 to 250° C., further preferably 160 to 240° C. If the reaction temperature is too low, it may cause the reaction rate to be low and thus the process, per se, to be impractical. Also, if the reaction temperature is too high, production of by-product comprising compounds with high boiling temperatures may be promoted, and thus the reaction efficiency may be unsatisfactory.

The temperatures of the portions of the liquid reaction mixture located in the series of reaction regions may be different from each other.

Preferably, the temperature of the portion of the liquid reaction mixture located in the frontmost reaction region is established at a relatively low level, and the temperature of the portion of the liquid reaction mixture located in the rearmost reaction region, in which the portion of the reaction mixture portion has a decreased content of non-reacted epoxycyclododecane compound, is equal to or higher than that of the frontmost reaction region. Namely, it is preferable that the temperature of a portion of the liquid reaction mixture located in the front part of the series of reaction regions be equal to or lower than that in the rear part of the series of reaction regions. The above-mentioned temperature control of the series of reaction regions enables a high conversion of the starting compound and a high selectivity to the target compound to be attained. Particularly, the reaction temperature of the liquid reaction mixture at an outlet portion of the rearmost reaction region is preferably controlled to 0 to 100° C., more preferably 1 to 50° C., above the temperature of a portion of the liquid reaction mixture at an outlet portion of the frontmost reaction region of the series of reaction regions.

The reasons by which the selectivity to the target compound is enhanced, are not fully clear. It is assumed that, since the resultant cyclododecanone compound exhibits a higher thermal stability at a high temperature than that of the starting epoxycyclododecane compound, the thermal deterioration of the epoxycyclododecane compound can be restricted with a high efficiency by keeping the temperature of the liquid reaction mixture at a relatively low level in the front part of the series of reaction regions and increasing the temperature of the liquid reaction mixture in the rear part of the series of reaction regions.

In the process of the present invention, there is no limitation to the reaction pressure. The isomerization reaction may be carried out under a pressure higher than the ambient air pressure, under ambient air pressure or under a reduced pressure.

The reaction time of the process of the present invention is variable in response to the content of the catalyst in the liquid reaction mixture, the reaction temperature and the member of the reaction regions in the series of reaction regions. usually, the reaction time is preferably 0.1 to 24 hours, more preferably 0.5 to 20 hours.

In the process of the present invention, the isomerization reaction of the epoxycyclododecane compound is usually carried out without using a reaction medium, namely, a solvent, because the starting epoxycyclododecane compound and the resultant cyclododecanone compound serve as a reaction medium. However, the isomerization reaction of the process of the present invention may be effected in a non-polar reaction medium.

The non-polar reaction medium comprises, for example, at least one cyclohydrocarbon having 6 to 12 carbon atoms, and is employed in a content not exceeding the content of the epoxycyclododecane compound in the liquid reaction mixture.

In the process of the present invention, the isomerization reaction of the epoxycyclododecane compound is carried out in a reactor comprising a plurality of reaction regions separated from each other and connected to each other in series through at least one liquid path.

In a conventional reactor as shown in FIG. 1, a starting liquid reaction mixture comprising an epoxycyclododecane compound, a catalyst and optionally a solvent is fed from a feed source (not shown) into a front part la of a sole reaction vessel 1 through a feed line 2, the fed reaction mixture moves from the front part 1a toward a rear part 1b of the reaction vessel 1, and is delivered from the rear part 1b through a delivery line 3.

In the conventional process as shown in FIG. 1, the conversion of the starting compound and the selectivity to the target compound are unsatisfactory.

In the process of the present invention, the isomerization reaction of an epoxycyclododecane compound in the presence of the above-mentioned specific catalyst is carried out by feeding a liquid reaction mixture comprising an epoxycyclododecane compound and a catalyst comprising at least one member selected from lithium bromide and lithium iodide into a frontmost reaction region of a plurality of reaction regions connected to each other in series; successively passing the liquid reaction mixture through the series of reaction regions to catalytically isomerize the epoxycyclododecane compound to produce a corresponding cyclododecanone compound; and collecting the resultant reaction mixture containing the cyclododecanone compound from a rearmost reaction region of the series of reaction regions.

In an embodiment of the process of the present invention, the series of reaction regions comprise a plurality of reaction vessels independent from each other and connected to each other in series in a manner such that with respect to a pair of front and back reaction vessels arranged adjacent to each other, the front vessel is connected to the back vessel through a conduit. In this embodiment, a bottom portion of the front vessel is connected to a top portion of the back vessel through the conduit.

Figure 2:
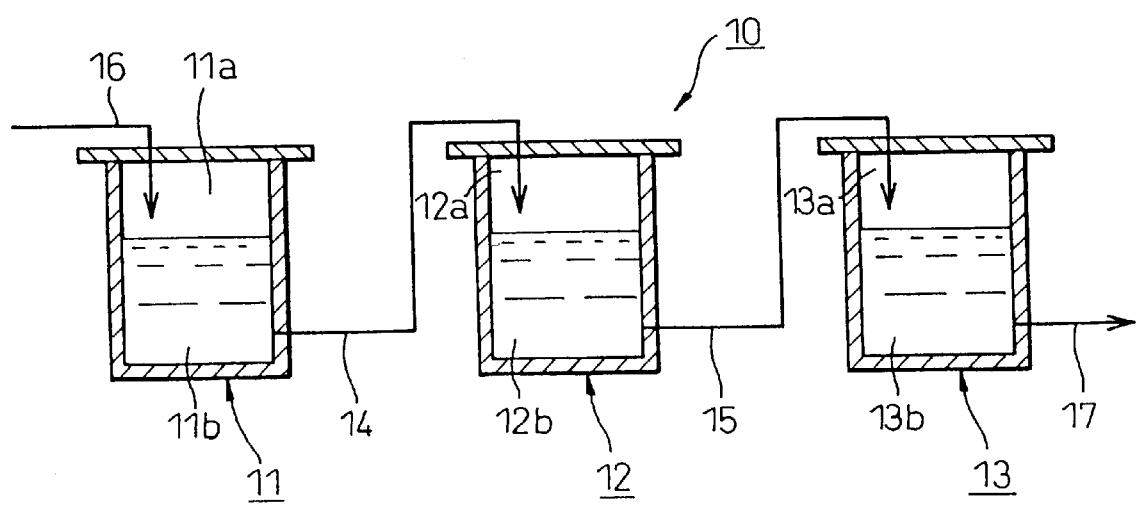
FIG. 2 is an explanatory cross-sectional view of an embodiment of the isomerization reactor usable for the process of the present invention.

A reactor usable for the embodiment is shown in FIG. 2.

In FIG. 2, a reactor 10 comprises a plurality of reaction vessels, for example three reaction vessels including a frontmost vessel 11, a middle vessel 12 and a rearmost vessel 13, which respectively provide reaction regions separated from each other. The reaction vessels 11, 12 and 13 are connected to each other in series through connection conduits 14 and 15. The frontmost reaction vessel 11 is connected at a top portion 11a thereof to a feed line 16 for feeding a liquid reaction mixture containing a starting epoxycyclododecane compound and a catalyst from a supply source (not shown) into the frontmost vessel 11.

The connection conduit 14 is connected at a front end thereof to a bottom portion 11b of the frontmost vessel 11 and at a rear end thereof to a top portion 12a of the middle vessel 12. Also, the connection conduit 15 is connected at a front end thereof to a bottom portion of the middle vessel 12b and at a rear end thereof to a top portion 13a of the rearmost vessel 13. A bottom portion 13b of the rearmost vessel 13 is connected to a delivery line 17 through which the resultant liquid reaction mixture containing the target compound is delivered to the outside of the reactor. The vessels 11, 12 and 13 may be completely closed as shown in FIG. 2 and may be completely filled with the liquid reaction mixture. Also, the upper portions 11a, 12a and 13a of the vessels may not be filled with the liquid reaction mixture as shown in FIG. 2, and at least one of the upper portions 11a, 12a, 13a, may be sealed with an inert gas. One or more of the conduits and the feed and delivery lines are optionally provided with a liquid-transporting means, for example, a liquid pump (not shown in FIG. 2).

In another embodiment of the process of the present invention, the series of reaction regions comprise a plurality of reaction chambers separated from each other and connected to each other in such a manner that, with respect to a pair of front and back reaction chambers arranged adjacent to each other, a top portion of the front vessel is connected to a top portion of the back vessel through a liquid path through which a portion of the liquid reaction mixture contained in the front vessel is allowed to overflow into the back vessel.

Figure 3:
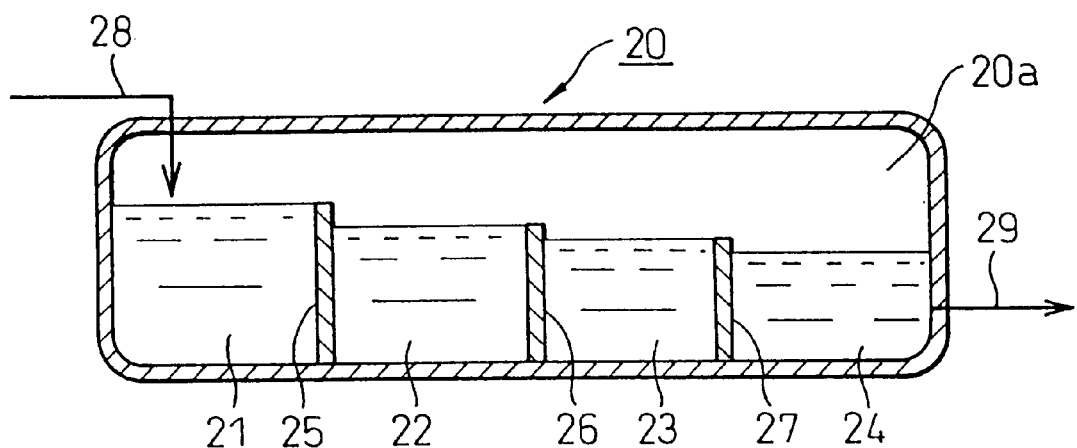
FIG. 3 is an explanatory cross-sectional view of another embodiment of the isomerization reactor usable for the process of the present invention.

For this embodiment, a reactor shown in FIG. 3 can be used.

In FIG. 3, a closed reaction vessel 20 is divided with partitions 25, 26 and 27 into a plurality of reaction chambers, for example, 4 reaction chambers 21, 22, 23 and 24, forming reaction regions. The frontmost chamber 21 is connected to a feed line 28 for feeding a starting liquid reaction mixture from a supply source (not shown), and the rearmost chamber 24 is connected to a delivery line 29 for delivering the resultant liquid reaction mixture containing the target compound. The top of the partition 25 in higher than the top of the partition 26 which is higher than the top of the partition 26 which is higher than the top of the partition 27. Thus, the liquid reaction mixture fed into the frontmost chamber 21 through the feed line 28 successively passes through the reaction chambers 21, 22, 23 and 24, while overflowing over the tops of the partitions 25, 26 and 27, and is finally delivered from the rearmost chamber 24 through the delivery line 29. The space of the reactor 20 above the liquid levels of the reaction chambers 21 to 24 may be filled with an inert gas to seal the reactor.

Namely, between a pair of reaction chambers adjacent to each other and separated from each other with a partition, a liquid path over the top of the partition is formed. The liquid path may be formed by a trough, a gutter or a pipe extending over the top of the partition.

In the reactor shown in FIG. 3, each of the partitions 25 to 27 may have at least one hole which can allow the liquid reaction mixture to pass therethrough at a total flow rate lower than the feed rate of the reaction mixture.

Figure 4:
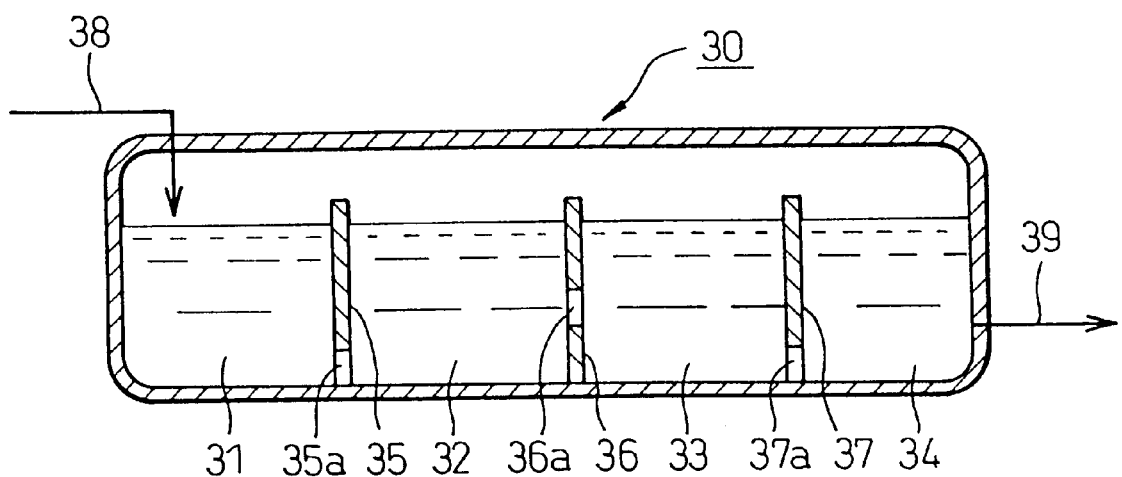
FIG. 4 is an explanatory cross-sectional view of still another embodiment of the isomerization reactor usable for the process of the present invention.

In still another embodiment of the present invention, the series of reaction regions comprise a plurality of reaction chambers separated from each other with partitions arranged between the reaction chambers and connected to each other in series through at least one hole formed in each of the partitions. In this embodiment, a reactor as shown in FIG. 4 can be used. In FIG. 4, the inside of the reactor 30 is partitioned into a plurality of reaction chambers, for example, 4 chambers 31, 32, 33 and 34, with partitions 35, 36 and 37 each having at least one of holes 35a, 36a and 37a through which the reaction chambers are connected to each other. The holes of the partitions form liquid paths. The partitions may be formed by perforated plates. The frontmost chamber 31 is connected to a feed line 38 through which a starting liquid reaction mixture is fed from a supply source (not shown) into the frontmost chamber 31. Also, the rearmost chamber 34 is connected to a delivery line 39 through which a resultant liquid reaction mixture containing a target compound is delivered from the rearmost chamber 34 to the outside of the reactor 30.

The liquid reaction mixture is fed into the frontmost chamber 31 through the feed line 38, successively passes through the separate reaction chambers 31 to 34 while passing through the holes 35a to 37a of the partitions 35 to 37, and the resultant liquid reaction mixture is delivered from the rearmost reaction chamber 34 through the delivery line 39.

In the reactor 30 of FIG. 4, the partitions may be the same, or different, in height as long as each reaction chamber has a satisfactory capacity for the liquid reaction mixture.

In the process of the present invention, there is no limitation to the number of the reaction regions as long as the reaction region number is 2 or more. Usually, the number of the reaction regions is preferably 2 to 30, more preferably 3 to 10.

Also, in the process of the present invention, optionally, the liquid reaction mixture is forcedly stirred in at least one reaction region by using a stirrer, a liquid circulation pump or a gas-bubbling means, or is gently stirred by the flow of the reaction mixture through the reaction regions or by a convection current in the reaction mixture, in each region.

The reactor may be heated by a conventional heating means, for example, a heating jacket through which a heating medium circulates.

In the process of the present invention, the use of the above-mentioned types of reactors enables the starting reaction mixture comprising an epoxycyclododecane compound and a catalyst (lithium bromide or lithium iodide) and fed through a feed line into a frontmost reaction region of the reactor, to continuously pass through a plurality of reaction regions connected to each other through the liquid paths to isomerize the epoxycyclododecane compound with a high conversion thereof and with a high selectivity to the target cyclododecanone compound in a relatively short time, and a resultant reaction mixture containing the target cyclododecanone compound in a high content to be collected from the rearmost reaction region of the reactor.

Since the cyclododecanone compounds and the corresponding epoxycyclododecane compounds are very close, in physical and chemical properties, to each other, it is usually difficult to separate and refine them by distillation, crystallization or extraction. Therefore, the non-reacted epoxycyclododecane compound and the target cyclododecanone compound contained in the liquid reaction mixture collected from the rearmost reaction region are very difficult to separate from each other. Thus, the content of the non-reacted epoxycyclododecane compound in the collected liquid reaction mixture is preferably controlled to 5% by weight or less, more preferably 2% by weight or less, still more preferably 1% by weight or less.

The resultant reaction mixture collected from the rearmost reaction region can be practically used as a target cyclododecanone compound product. If necessary, in view of the use, the collected cyclododecanone compound product is refined by, for example, distillation to remove the high boiling temperature impurities (by-products).

There is no limitation to the type of materials for forming the reactor of the process of the present invention. For example, the reactor can be made from glass or stainless steel.

EXAMPLES

The present invention will be further illustrated by the following examples.

(1) In the examples and comparative examples, the starting material and the resultant product were analyzed as follows.

The starting material and the resultant product were quantitatively analyzed by gas chromatography using a capillary column in accordance with the internal standard method.

(2) Since the molecular weight of the starting epoxycyclododecane compound is equal to that of the resultant cyclododecanone compound corresponding to the starting compound, the conversion of the epoxycyclododecane compound (percentage of the molar amount of the consumed epoxycyclododecane compound based on the molar amount of the supplied epoxycyclododecane compound), the selectivity to the cyclododecanone compound (percentage of the molar amount of the produced cyclododecanone compound based on the molar amount of the consumed epoxycyclododecane compound), the yield of the cyclododecanone compound (a percentage of the molar amount of the produced cyclododecanone compound based on the molar amount of the supplied epoxycyclododecane compound) are calculated on the basis of weight of the compounds.

Example 1

A glass reactor having the constitution as shown in FIG. 3 was employed. In the reactor, four reaction chambers 21, 22, 23 and 24 were provided. The liquid capacities of the frontmost chamber 21, the front next chamber 22, the rear next chamber 23 and rearmost chamber 24 were 27 ml, 24 ml, 22 ml and 46 ml and the total liquid capacity of the reactor was 119 ml. The chambers 21 to 24 were partitioned from each other with glass partition plates 25, 26 and 27, having no perforation.

A starting liquid reaction mixture comprising 98.3% by weight of epoxycyclododecane, 0.2% by weight of cyclododecanone and 0.35% by weight of lithium iodide (corresponding to 0.4 molar % based on the molar amount of the epoxycyclododecane) and the balance consisting of impurities, was continuously fed into the frontmost chamber 21 of the reactor, through the feed line 28 at a feed rate of 35 ml/hr by using a liquid transportation pump (not shown in FIG. 3). The reactor is placed in an oil bath heated at a temperature of 230° C.

The fed liquid reaction mixture successively passed through the chambers 21 to 24 while overflowing the tops of the partition plates 25 to 27, and while nitrogen gas was passed through the upper space 20a of the reactor, to catalytically isomerize the epoxycyclododecane into cyclododecanone.

In each reaction chamber, the liquid reaction mixture was stirred by a stirrer (not shown in FIG. 3).

Finally, the resultant liquid reaction mixture was delivered from the rearmost chamber 24 through the delivery line 29. The average staying time of the liquid reaction mixture in the reactor was 3.4 hours, and the average temperature of the reaction mixture in each of the reaction chambers 21 to 24 was 230° C.

After the above-mentioned reaction procedure reached a stable condition, the delivered reaction mixture was cooled to room temperature. A sample of the cooled reaction mixture in an amount of 0.1 g was dissolved in 10 ml of toluene and the solution was subjected to gas chromatographic analysis.

In the analysis results, it was confirmed that the delivered liquid reaction mixture contained 96.5% by weight of cyclododecanone and 0.3% by weight of non-reacted epoxycyclododecane. Thus, in the isomerization reaction, the conversion of epoxycyclododecane was 99.7% and the selectivity to cyclododecanone was 98.3%.

Example 2

Cyclododecanone was prepared by the same procedures and reactor as in Example 1, except that the fed liquid reaction mixture comprised 98.0% by weight of epoxycyclododecane, 0.2% by weight of cyclododecanone and 0.64% by weight of lithium iodide (corresponding to 0.88 molar % based on the molar amount of epoxycyclododecane), the feed rate was 33 ml/hr, the average reaction temperature in each of the reaction chambers was 200° C., the total capacity of the reaction chambers was 90 ml.

According to the gas chromatographic analysis, the resultant reaction mixture delivered from the rearmost chamber 24 comprised 96.2% by weight of cyclododecanone and 0.8% by weight of non-reacted epoxycyclododecane. Thus, the conversion of epoxycyclododecane was 99.2% and the selectivity of cyclododecanone was 98.8%.

The average staying time of the reaction mixture in the reactor was 2.7 hours and the reaction temperature in each of the reaction chambers 21 to 24 was 200° C.

Example 3

Cyclododecanone was prepared by the same procedures and reactor as in Example 1, except that the fed liquid reaction mixture comprised 98.1% by weight of epoxycyclododecane, 0.2% by weight of cyclododecanone and 0.47% by weight of lithium bromide (corresponding to 1.0 molar % based on the molar amount of epoxycyclododecane), the feed rate was 36 ml/hr, the average reaction temperature in each of the reaction chambers was 230° C., the total capacity of the reaction chambers was 85 ml.

According to the gas chromatographic analysis, the resultant reaction mixture delivered from the rearmost chamber 24 comprised 90.5% by weight of cyclododecanone and 2.8% by weight of non-reacted epoxycyclododecane. Thus, the conversion of epoxycyclododecane was 97.1% and the selectivity of cyclododecanone was 94.8%.

The average staying time of the reaction mixture in the reactor was 2.4 hours and the reaction temperature in each of the reaction chambers 21 to 24 was 230° C.

Example 4

A reactor having glass reaction vessels 11 to 13 as shown in FIG. 2 was employed. Each vessel had a capacity of 50 ml.

A liquid reaction mixture comprising 97.9% by weight of epoxycyclododecane, 0.2% by weight of cyclododecanone, 0.68% by weight of lithium iodide (corresponding to 0.94 molar % based on the molar amount of epoxycyclododecane) and the balance consisting of impurities was continuously fed at a feed rate of 42 ml/hr into a frontmost vessel 11 of the reactor through a fixed delivery pump. The fed liquid reaction mixture successively passed through the frontmost vessel 11, the conduit 14, the middle vessel 12, the conduit 15 and the rearmost vessel 13, to isomerize epoxycyclododecane. The average residence time of the reaction mixture in the reactor was 3.6 hours. Finally, the resultant reaction mixture was delivered from the rearmost vessel 13 through the delivery line 17.

In each of the reaction vessels 11 to 13, the reaction mixture was stirred by a stirrer (not shown in FIG. 2) and the temperature of the reaction mixture was controlled to 200° C.

After the reaction procedures of the liquid reaction mixture in the reactor was stabilized, a sample of the delivered reaction mixture was cooled to room temperature and dissolved in a concentration of 10 g/liter in toluene and subjected to the gas chromatographic analysis. By analysis, it was confirmed that the delivered reaction mixture comprised 96.1% by weight of cyclododecanone, and 0.6% by weight of epoxycyclododecane, and the conversion of epoxycyclododecane was 99.4% and the selectivity to cyclododecanone was 98.6%.

Example 5

Cyclododecanone was prepared by the same reaction procedures and reactor as in Example 4, except that the fed liquid reaction mixture comprised 98.8% by weight of 1,2-epoxy-5,9-cyclododecadiene, 0.70% by weight of lithium iodide (corresponding to 0.95 molar % based on the molar amount of 1,2-epoxy-5,9-cyclododecadiene) and the balance consisting of impurities.

According to the analysis, it was confirmed that the delivered reaction mixture comprised 96.6% weight of 1-oxo-5,9-cyclododecadiene and 0.3% by weight of 1,2-epoxy-5,9-cyclododecadiene, and the conversion of 1,2-epoxy-5,9-cyclododecadiene was 99.7% and the selectivity to 1-oxo-5,9-cyclododecadiene was 98.1%. The average staying time of the reaction mixture in the reactor was 3.6 hours.

Example 6

Cyclododecanone was prepared by the same reaction procedures and reactor as in Example 4, except that the reaction temperature of the frontmost vessel was 180° C., the reaction temperature of the middle vessel was 200° C. and the reaction temperature of the rearmost temperature was 220° C.

According to the analysis, it was confirmed that the delivered reaction mixture comprised 97.4% weight of cyclododecanone and 0.1% by weight of epoxycyclododecane, and the conversion of epoxycyclododecane was 99.9% and the selectivity to cyclododecanone was 99.4%.

The average staying times of the reaction mixture in the frontmost, middle and rearmost vessels were each 1.2 hours and the average total staying time was 3.6 hours.

Comparative Example 1

A glass reactor as shown in FIG. 1 was employed. The glass reactor 1 had a single reaction region. The liquid reaction mixture comprising 98.2% by weight of epoxycyclododecane, 0.2% by weight of cyclododecanone and 0.42% by weight of lithium iodide (corresponding to 0.58 molar % based on the molar amount of epoxycyclododecane) and the balance consisting of impurities was fed into the reactor through a feed line 2 at a feed rate of 31 ml/hr at a reaction temperature of 230° C. so that the liquid reaction mixture is contained in an amount of 105 ml in the reactor 1, while passing a nitrogen gas through a space above the level of the liquid reaction mixture contained in the reactor 1, to isomerize epoxycyclododecane, under reaction conditions similar to those in Example 1. The liquid reaction mixture delivered from the reactor through a delivery line 3 was subjected to gas chromatographic analysis. According to the analysis, it was confirmed that the resultant liquid reaction mixture comprised 89.0% by weight of cyclododecanone, 3.1% by weight of epoxycyclododecane, the conversion of epoxycyclododecane was 96.8% and the selectivity to cyclododecanone was 93.4%.

The average staying time of the liquid reaction mixture in the reactor was 3.4 hours.

Comparative Example 2

A glass reactor as shown in FIG. 1 was employed. The glass reactor 1 had a single reaction region. The liquid reaction mixture comprising 97.9% by weight of epoxycyclododecane, 0.2% by weight of cyclododecanone and 0.70% by weight of lithium iodide (corresponding to 0.97 molar % based on the molar amount of epoxycyclododecane) and the balance consisting of impurities, was fed into the reactor through a feed line 2 at a feed rate of 35 ml/hr at a reaction temperature of 200° C. so that the liquid reaction liquid is contained in an amount of 105 ml in the reactor, while passing a nitrogen gas through a space above the level of the liquid reaction mixture contained in the reactor 1, to isomerize epoxycyclododecane, under reaction conditions similar to those in Example 2. The liquid reaction mixture delivered from the reactor through a delivery line 3 was subjected to the gas chromatographic analysis. According to the analysis, it was confirmed that the resultant liquid reaction mixture comprised 86.9% by weight of cyclododecanone, 6.8% by weight of epoxycyclododecane, the conversion of epoxycyclododecane was 93.1% and the selectivity to cyclododecanone was 95.2%.

The average staying time of the liquid reaction mixture in the reactor was 3.0 hours.

Comparative Example 3

A glass reactor as shown in FIG. 1 was employed. The glass reactor 1 had a single reaction region. The liquid reaction mixture comprising 98.1% by weight of epoxycyclododecane, 0.2% by weight of cyclododecanone and 0.47% by weight of lithium bromide (corresponding to 1.0 molar % based on the molar amount of epoxycyclododecane) and the balance consisting of impurities was fed into the reactor through a feed line 2 at a feed rate of 36 ml/hr at a reaction temperature of 230° C. so that the liquid reaction mixture is contained in an amount of 105 ml in the reactor 1, while passing a nitrogen gas through a space above the level of the fed liquid reaction mixture located in the reactor 1, to isomerize epoxycyclododecane, under reaction conditions similar to those in Example 3. The liquid reaction mixture delivered from the reactor through a delivery line 3 was subjected to the gas chromatographic analysis. According to the analysis, it was confirmed that the resultant liquid reaction mixture comprised 77.8% by weight of cyclododecanone, 12.7% by weight of epoxycyclododecane, the conversion of epoxycyclododecane was 87.1% and the selectivity of cyclododecanone was 90.9%.

The average staying time of the liquid reaction mixture in the reactor was 2.9 hours.

The reaction conditions and analysis results of Examples 1 to 6 and Comparative Examples 1 to 3 are shown in Table 1.

TABLE 1

| Example No. | Item | Reaction condition | | | | | Analysis results | |
|---|---|---|---|---|---|---|---|---|
| | | The number of reaction regions | Feed rate (ml/hr) | Catalyst (molar %) | Reaction temperature (° C.) | Residence time (hr) | Starting compound (conversion, %) | Resultant compound (Selctivity, %) |
| Example | 1 | 4 | 35 | LiI (0.49) | 230 | 3.4 | ECD (99.7) | CDON (98.3) |
| Comparative Example | 1 | 1 | 31 | LiI (0.58) | 230 | 3.4 | ECD (96.8) | CDON (93.4) |
| Example | 2 | 4 | 33 | LiI (0.88) | 200 | 2.7 | ECD (99.2) | CDON (98.8) |
| Comparative Example | 2 | 1 | 35 | LiI (0.97) | 200 | 3.0 | ECD (93.1) | CDON (95.2) |
| Example | 3 | 4 | 36 | LiBr (1.0) | 230 | 2.4 | ECD (97.1) | CDON (94.8) |
| Comparative Example | 3 | 1 | 36 | LiBr (1.0) | 230 | 2.9 | ECD (87.1) | CDON (90.9) |
| Example | 4 | 3 | 42 | LiI (0.94) | 200 | 3.6 | ECD (99.4) | CDON (98.6) |
| | 5 | 3 | 42 | LiI (0.95) | 200 | 3.6 | ECD" (99.7) | CDDE (98.1) |

TABLE 1-continued

| Example No. | Item | Reaction condition ||||| Analysis results ||
|---|---|---|---|---|---|---|---|---|
| | | The number of reaction regions | Feed rate (ml/hr) | Catalyst (molar %) | Reaction temperature (° C.) | Residence time (hr) | Starting compound (conversion, %) | Resultant compound (Selctivity, %) |
| 6 | | 3 | 42 | LiI (0.94) | 180–220 | 3.6 | ECD (99.9) | CDON (99.4) |

Note:
ECD . . . Epoxycyclododecane
CDON . . . Cyclododecanone
ECD" . . . 1,2-Epoxy-5,9-cyclododecadiene
CDDE . . . 1-Oxo-5,9-cyclododecadiene
All the reaction procedures in the examples and comparative examples were carried out in an inert gas atmosphere.

INDUSTRIAL APPLICABILITY

The process of the present invention enables a cyclododecanone compound to be continuously produced from a corresponding epoxycyclododecane compound in an industrial scale within a relatively short reaction time with a high conversion of the epoxycyclododecane compound and with a high selectivity to the cyclododecanone compound.

What is claimed is:

1. A process for continuously producing a cyclododecanone compound, comprising
   feeding a liquid reaction mixture comprising an epoxycyclododecane compound and a catalyst comprising at least one member selected from lithium bromide and lithium iodide without using a reaction medium, into a frontmost reaction region of a plurality of reaction regions connected to each other in series;
   successively passing the liquid reaction mixture through the series of reaction regions to catalytically isomerize the epoxycyclododecane compound to produce a corresponding cyclododecanone compound; and
   collecting the resultant reaction mixture containing the cyclododecanone compound from a rearmost reaction region of the series of reaction regions, wherein during the feeding and successive passing procedures, the starting epoxycyclododecane compound and the resultant cyclododecanone compound serve as a reaction medium.

2. The process for continuously producing a cyclododecanone compound as claimed in claim 1, wherein the epoxycyclododecane compound is selected from saturated and unsaturated cycloaliphatic compounds having 12 carbon atoms and provided with an epoxy group.

3. The process for continuously producing a cyclododecanone compound as claimed in claim 1, wherein the epoxycyclododecane compound is selected from monoepoxycyclododecane, monoepoxycyclododecenes, monoepoxycyclododecadienes or monoepoxycyclododecatrienes.

4. The process for continuously producing a cyclododecanone compound as claimed in claim 1, wherein the temperature of a portion of the liquid reaction mixture located in a rear part of the series of reaction regions is controlled to be equal to, or higher than, that in a front part of the series of reaction regions.

5. The process for continuously producing a cyclododecanone compound as claimed in claim 1, wherein the series of reaction regions are constituted from a plurality of reaction vessels independent from each other and connected to each other in series in such a manner that, with respect to a pair of front and back reaction vessels arranged adjacent to each other, the front vessel is connected to the back vessel through a conduit.

6. The process for continuously producing a cyclododecanone compound as claimed in claim 5, wherein a bottom portion of the front vessel is connected to a top portion of the back vessel through the conduit.

7. The process for continuously producing a cyclododecanone compound as claimed in claim 1, wherein the series of reaction regions are constituted from a plurality of reaction chambers separated from each other and connected to each other in such a manner that, with respect to a pair of front and back reaction chambers arranged adjacent to each other, a top portion of the front vessel is connected to a top portion of the back vessel through a liquid path through which a portion of the liquid reaction mixture contained in the front vessel is allowed to overflow into the back vessel.

8. The process for continuously producing a cyclododecanone compound as claimed in claim 1, wherein the series of reaction regions comprise a plurality of reaction chambers separated from each other by partitions arranged between the reaction chambers and connected to each other in series through at least one hole formed in each of the partitions.

9. The process for continuously producing a cyclododecanone compound as claimed in claim 1, wherein at least one of the reaction region is sealed with an inert gas.

10. The process for continuously producing a cyclododecanone compound as claimed in claim 1, wherein the catalyst is present in an amount of 0.01 to 20 molar % based on the molar amount of the epoxycyclododecane compound.

11. The process for continuously producing a cyclododecanone compound as claimed in claim 1, wherein the liquid reaction mixture in the series of reaction regions is heated to a temperature of 100 to 350° C.

12. The process for continuously producing a cyclododecanone compound as claimed in claim 11, wherein the temperature of the liquid reaction mixture located at the outlet portion of the rearmost reaction region is controlled to 0 to 100° C. above that at the outlet portion of the frontmost reaction region.

13. The process for continuously producing a cyclododecanone compound as claimed in claim 1, wherein the liquid reaction mixture passes through the series of reaction regions in a time of 0.1 to 24 hours.

\* \* \* \* \*